(12) United States Patent
Kumta et al.

(10) Patent No.: US 9,510,932 B2
(45) Date of Patent: Dec. 6, 2016

(54) BIODEGRADABLE METAL ALLOYS

(71) Applicant: UNIVERSITY OF PITTSBURGH-OF THE COMMONWEALTH SYSTEM OF HIGHER EDUCATION, Pittsburgh, PA (US)

(72) Inventors: Prashant N. Kumta, Pittsburgh, PA (US); Da-Tren Chou, Pittsburgh, PA (US); Daeho Hong, Pittsburgh, PA (US); Partha Saha, Pittsburgh, PA (US)

(73) Assignee: University of Pittsburgh-Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 14/349,564

(22) PCT Filed: Oct. 5, 2012

(86) PCT No.: PCT/US2012/058939
§ 371 (c)(1),
(2) Date: Apr. 3, 2014

(87) PCT Pub. No.: WO2013/052791
PCT Pub. Date: Apr. 11, 2013

(65) Prior Publication Data
US 2014/0248288 A1    Sep. 4, 2014

Related U.S. Application Data

(60) Provisional application No. 61/544,127, filed on Oct. 6, 2011.

(51) Int. Cl.
| | | |
|---|---|---|
| *A61F 2/02* | (2006.01) | |
| *C22C 23/00* | (2006.01) | |
| *C22C 23/04* | (2006.01) | |
| *C22C 23/06* | (2006.01) | |
| *C22C 1/02* | (2006.01) | |
| *C22F 1/06* | (2006.01) | |
| *A61L 27/04* | (2006.01) | |
| *A61L 27/58* | (2006.01) | |
| *A61K 31/397* | (2006.01) | |
| *A61K 31/7036* | (2006.01) | |

(52) U.S. Cl.
CPC .............. *A61F 2/02* (2013.01); *A61K 31/397* (2013.01); *A61K 31/7036* (2013.01); *A61L 27/047* (2013.01); *A61L 27/58* (2013.01); *C22C 1/02* (2013.01); *C22C 23/00* (2013.01); *C22C 23/04* (2013.01); *C22C 23/06* (2013.01); *C22F 1/06* (2013.01)

(58) Field of Classification Search
CPC ............ A61F 2/02; C22C 23/00; C22C 23/04; C22C 23/06; C22C 1/02; A61K 31/397; A61K 31/7036; A61K 33/24; A61K 33/30; A61K 33/32; A61K 33/38; A61L 27/047; A61L 27/58; C22F 1/06
See application file for complete search history.

(56) References Cited

U.S. PATENT DOCUMENTS

| | | | |
|---|---|---|---|
| 8,293,031 | B2 | 10/2012 | Gerold et al. |
| 8,435,281 | B2 | 5/2013 | Weber |
| 2007/0227629 | A1 | 10/2007 | Gerold et al. |
| 2008/0031765 | A1 | 2/2008 | Gerold et al. |
| 2008/0033530 | A1 | 2/2008 | Zberg et al. |
| 2009/0081313 | A1 | 3/2009 | Aghion et al. |
| 2011/0192500 | A1 | 8/2011 | Uggowitzer et al. |
| 2013/0144290 | A1 | 6/2013 | Schiffl et al. |
| 2013/0195714 | A1 | 8/2013 | Lyon |

FOREIGN PATENT DOCUMENTS

| | | |
|---|---|---|
| JP | 08027533 | 1/1996 |
| KR | 1020080027202 | 3/2008 |
| KR | 1020110065390 A | 6/2011 |

OTHER PUBLICATIONS

Huinan Liu, "Nanotechnology Enabled in situ Sensors for Monitoring Health; Chapter 6: Biodegradable Metals and Responsive Biosensors for Musculoskeletal Applications" 2010, Springer Science & Business Media, vol. 68 of The new synthase historical library, p. 115-137.*
Won-Wook Park et al., "Microstructural change and precipitation hardening in melt-spun MG-X-Ca alloys", Science and Technology of Advanced Materials (2001), 2, 73-78.*

* cited by examiner

*Primary Examiner* — Sue Liu
*Assistant Examiner* — Nathan W Schlientz
(74) *Attorney, Agent, or Firm* — Eckert Seamans Cherin & Melloyy, LLC; Carol A. Marmo

(57) ABSTRACT

The invention relates to biodegradable, metal alloy-containing compositions, methods for their preparation and applications for their use. The compositions include magnesium and other components, such as yttrium, calcium, silver, cerium, and zirconium; or zinc, silver, cerium, and zirconium; or aluminum, zinc, calcium, manganese, silver, yttrium; or strontium, calcium, zinc. The compositions are prepared by vacuum induction/crucible melting together the components and casting the melted mixture in a preheated mild steel/copper mold. In certain embodiments, the compositions of the invention are particularly useful for forming medical devices for implantation into a body of a patient.

14 Claims, No Drawings

BIODEGRADABLE METAL ALLOYS

The invention was made with government support under EEC-0812348 awarded by the National Science Foundation. The government has certain rights in the invention.

FIELD OF THE INVENTION

The invention relates to metal alloy-containing compositions and articles, and methods for their preparation. The invention is particularly suitable for use in fabricating biodegradable materials and medical devices for implantation into a body of a patient, such as for example, orthopedic, craniofacial and cardiovascular implant devices.

BACKGROUND OF THE INVENTION

Metallic implant devices, such as plates, screws, nails and pins are commonly used in the practice of orthopedic, craniofacial and cardiovascular implant surgery. Furthermore, metallic stents are also implanted into a body of a patient to support lumens, for example, coronary arteries. Most of these metallic implant devices which are currently used are constructed of stainless steel, cobalt-chromium (Co—Cr) or titanium alloys. Advantageously, these materials of construction exhibit good biomechanical properties. However, disadvantageously, implant devices constructed of these materials do not degrade over a period of time. Thus, surgery may be required when there is no longer a medical need for the implant device and when, for various reasons, it may be desired to remove the implant device from a body of a patient. For example, in certain instances, such as pediatric applications, there may be a concern that if an implant device is not removed, it may eventually be rejected by the body and cause complications for the patient. Thus, it would be advantageous for: (i) the implant device to be constructed of a material that is capable of degrading over a period of time, (ii) for the implant device to dissolve in a physiological environment such that it would not remain in the body when there is no longer a medical need for it, and (iii) surgery not to be required to remove the implant device from the body of the patient.

Currently, biomaterials used for orthopedic, craniofacial and cardiovascular applications are primarily chosen based on their ability to withstand cyclic load-bearing. Metallic biomaterials in particular have appropriate properties such as high strength, ductility, fracture toughness, hardness, corrosion resistance, formability, and biocompatibility to make them attractive for most load bearing applications. The most prevalent metals for load-bearing applications are stainless steels, Ti, and Co—Cr based alloys, though their stiffness, rigidity, and strength far exceed those of natural bone. Their elastic modulus differs significantly from bone, causing stress-shielding effects that may lead to reduced loading of bone—with this decrease in stimulation resulting in insufficient new bone growth and remodeling, decreasing implant stability. Current metallic biomaterials also suffer from the risk of releasing toxic metallic ions and particles through corrosion or wear causing implant site immune response. They may also lead to hypersensitivity, growth restriction (most significantly for pediatric implants), implant migration, and imaging interference. Due to these complications, it is estimated that 10% of patients will require a second operation for the removal of permanent metallic plates and screws, exposing patients to additional risks, and increasing surgical time and resources.

Based on at least these issues, there is a desire to design and develop a new class of load-bearing biomaterials with the goal of providing adequate support while the bone is healing that harmlessly degrades over time.

To avoid complications associated with permanent fixation implants, degradable biomaterials have recently been developed. However, resorbable polymer fixation plates and screws are relatively weaker and less rigid compared to metals, and have demonstrated local inflammatory reactions. For example, biodegradable materials which are currently used in the construction of implant devices include polymers, such as polyhydroxy acids, polylactic acid (PLA), polyglycolic acid (PGA), and the like. These materials, however, have been found to exhibit relatively poor strength and ductility, and have a tendency to react with human tissue which can limit bone growth.

Magnesium alloys have recently emerged as a new class of biodegradable materials for orthopedic applications with more comparable properties to natural bone. Magnesium is known to be a non-toxic metal element that degrades in a physiological environment and therefore, may be considered a suitable element for use in constructing biodegradable implant devices. Magnesium is attractive as a biomaterial for several reasons. It is very lightweight, with a density similar to conical bone, and much less than stainless steel, titanium alloys, and Co—Cr alloys. The elastic modulus of magnesium is much closer to natural bone compared to other commonly used metallic implants, thus reducing the risk of stress shielding. Magnesium is also essential to human metabolism, is a cofactor for many enzymes, and stabilizes the structures of DNA and RNA. Most importantly, magnesium degrades to produce a soluble, non-toxic corrosion hydroxide product which is harmlessly excreted through urine. Unfortunately, accelerated corrosion of magnesium alloys may lead to accumulation of hydrogen gas pockets around the implant as well as insufficient mechanical performance and implant stability throughout the degradation and tissue healing process. The degradation of magnesium in a physiological environment yields magnesium hydroxide and hydrogen gas. This process is known in the art as magnesium corrosion. The hydrogen gas produced in the body of the patient as a result of magnesium corrosion can produce complications because the ability of the human body to absorb or release hydrogen gas is limited.

The various biodegradable metallic alloys known in the art may exhibit low biocompatibility and/or high corrosion rates, which render these materials unsuitable for use in medical applications, such as implant devices. Further, compositions of matter for use as implant devices should not include toxic elements, such as zinc and aluminum, or at least include these elements only in non-toxic amounts. Moreover, the composition should exhibit a corrosion rate that is suitable for implantation in a physiological environment, i.e., a body of a patient.

In the field of biomedical applications, there is a desire to develop biodegradable metal alloy-containing implant materials having good compressive strength with improved corrosion resistance and biocompatibility. Further, it is desirable to control the corrosion resistance and the hydrogen evolution therefrom, which is associated with the presence of magnesium in a physiological environment.

SUMMARY OF THE INVENTION

In one aspect, the invention provides a biodegradable, metal alloy-containing composition including from about 0.5 weight percent to about 4.0 weight percent of yttrium, from greater than zero to about 1.0 weight percent of calcium, from about 0.25 weight percent to about 1.0 weight percent of zirconium, and a balance of magnesium, based on the total weight of the composition. In certain embodiments, the metal alloy-containing composition can include about 1.0 weight percent of yttrium. In another embodiment, the metal alloy-containing composition can include about 1.0 weight percent of calcium. In still another embodiment, the metal alloy-containing composition can include less than about 0.5 weight percent of zirconium.

In another aspect, the invention provides a biodegradable, metal alloy-containing composition including from about 1.0 weight percent to about 6.0 weight percent of zinc, from greater than zero to about 1.0 weight percent of zirconium, and a balance of magnesium, based on the total weight of the composition. In certain embodiments, the metal alloy-containing composition can include about 4.0 weight percent of zinc. In another embodiment, the metal alloy-containing composition can include less than about 0.5 weight percent of zirconium.

In another aspect, the invention provides a method of preparing a biodegradable, metal alloy-containing composition including melting from about 0.5 weight percent to about 4.0 weight percent of yttrium, from greater than zero to about 1.0 weight percent of calcium, from about 0.25 weight percent to about 1.0 weight percent of zirconium, and a balance of magnesium, based on the total weight of the composition, to obtain a melted mixture and casting the melt mixture to obtain said biodegradable, metal alloy-containing composition. In certain embodiments, the method can include melting about 1.0 weight percent of yttrium. In another embodiment, the method can include melting about 1.0 weight percent of calcium. In still another embodiment, the method can include melting less than about 0.5 weight percent of zirconium.

In another aspect, the invention provides a method of preparing a biodegradable, metal alloy-containing composition including melting from about 1.0 weight percent to about 6.0 weight percent of zinc, from greater than zero to about 1.0 weight percent of zirconium, and a balance of magnesium, based on the total weight of the composition, to obtain a melted mixture and casting the melt mixture to obtain said biodegradable, metal alloy-containing composition. In certain embodiments, the method can include melting about 4.0 weight percent of zinc. In another embodiment, the method can include melting less than about 0.5 weight percent of zirconium.

In yet another aspect, the invention includes a biodegradable, metal alloy-containing article including a magnesium-containing composition including from about 0.5 weight percent to about 4.0 weight percent of yttrium, from greater than zero to about 1.0 weight percent of calcium, from about 0.25 weight percent to about 1.0 weight percent of zirconium, and a balance of magnesium, based on the total weight of the composition. In certain embodiments, the magnesium-containing composition can include about 1.0 weight percent of yttrium. In another embodiment, the magnesium-containing composition can include about 1.0 weight percent of calcium. In still another embodiment, the magnesium-containing composition can include less than about 0.5 weight percent of zirconium.

In yet another aspect, the invention includes a biodegradable, metal alloy-containing article including a magnesium-containing composition including from about 1.0 weight percent to about 6.0 weight percent of zinc, from greater than zero to about 1.0 weight percent of zirconium, and a balance of magnesium, based on the total weight of the composition. In certain embodiments, the magnesium-containing composition can include about 4.0 weight percent of zinc. In another embodiment, the magnesium-containing composition can include less than about 0.5 weight percent of zirconium.

In still another aspect, the invention includes a biodegradable, metal alloy-containing medical device including a magnesium-containing composition including about 0.5 weight percent to about 4.0 weight percent of yttrium, from greater than zero to about 1.0 weight percent of calcium, from about 0.25 weight percent to about 1.0 weight percent of zirconium, and a balance of magnesium, based on the total weight of the composition. In certain embodiments, the magnesium-containing composition can include about 1.0 weight percent of yttrium. In another embodiment, the magnesium-containing composition can include about 1.0 weight percent of calcium. In still another embodiment, the magnesium-containing composition can include less than about 0.5 weight percent of zirconium. In certain embodiments, this medical device can be implantable in a body of a patient. In another embodiment, the medical device can be an orthopedic device. In yet another embodiment, the medical device can be a craniofacial device. In still another embodiment, the medical device can be a cardiovascular device.

In still another aspect, the invention includes a biodegradable, metal alloy-containing medical device including a magnesium-containing composition including about 1.0 weight percent to about 6.0 weight percent of zinc, from greater than zero to about 1.0 weight percent of zirconium, and a balance of magnesium, based on the total weight of the composition. In certain embodiments, the magnesium-containing composition can include about 4.0 weight percent of zinc. In another embodiment, the magnesium-containing composition can include less than about 0.5 weight percent of zirconium. In certain embodiments, this medical device can be implantable in a body of a patient. In another embodiment, the medical device can be an orthopedic device. In yet another embodiment, the medical device can be a craniofacial device. In still another embodiment, the medical device can be a cardiovascular device.

DETAILED DESCRIPTION OF THE PREFERRED EMBODIMENTS

The invention relates to novel, biodegradable metal alloy-containing compositions. Further, the invention relates to articles, such as medical devices for implantation into a body of a patient, which are constructed or fabricated from the biodegradable metal alloy-containing compositions of the invention. Moreover, the invention relates to methods of preparing these biodegradable, metal alloy-containing compositions and articles for use in medical applications, such as but not limited to, orthopedic, craniofacial and cardiovascular surgery.

In addition to the biodegradability of the metal alloy-containing compositions of the invention, these compositions include at least one of the following characteristics: biocompatibility, corrosion resistance, cell attachment, viability and mechanical strength, which make them suitable for use as implant devices in a body of a patient.

In certain embodiments, the biodegradable, metal alloy-containing compositions of the invention are based on the presence of magnesium. The amount of magnesium and additional components are selected such that the compositions exhibit the characteristics identified herein. For example, components and their amounts are selected such that the compositions exhibit corrosion resistance in the presence of water and simulated body fluids which allow the compositions to be suitable for in vitro use, for example, in a physiological environment, such as a body of a patient.

In other embodiments, the biodegradable, metal alloy-containing compositions of the invention are prepared using selected components in specified amounts such that the compositions exhibit corrosion resistance with minimal or no evolution of hydrogen gas. The evolution of hydrogen, such as, hydrogen bubbles may result in complications within a body of a patient.

This invention includes controlling the corrosion rate and improving mechanical properties of magnesium alloys through the introduction of alloying elements and processing conditions. Magnesium corrosion and mechanical properties are strongly affected by alloying elements in the solid solution.

In certain embodiments, the biodegradable, metal alloy-containing compositions of the invention include the following components: yttrium, calcium, zirconium and magnesium. The amount of each of these components in the compositions can vary. In general, the amounts of each of these components are selected in order that the resulting compositions are within acceptable non-toxic limits such that the compositions are sufficiently biocompatible for implantation into a body of a patient, and are degradable over a period of time so that the implantation device does not remain in the body of the patient for prolonged periods of time, e.g., not beyond the period of time when there is a medical need for the implantation device. An implantation device fabricated in accordance with the invention will degrade and preferably completely dissolve within an acceptable time frame. For example, an implant device fabricated in accordance with the invention can serve as filler or support material during a bone healing process and following completion of this process, the implant device will degrade within an acceptable time period and therefore, will not remain in the body for a prolonged period of time. The acceptable non-toxic limits and the acceptable time frame for degradation can vary and can depend on particular physical and physiological characteristics of the patient, the particular in vive site of the implantation device, and the particular medical use of the implantation device.

In certain embodiments, the composition of the invention includes from about 0.5 weight percent to about 4.0 weight percent of yttrium, from greater than zero to about 1.0 weight percent of calcium, from about 0.25 weight percent to about 1.0 weight percent of zirconium, and the remainder or balance being magnesium based on the total weight of the composition. In other embodiments, the composition can include about 1.0 weight percent of yttrium or about 4.0 weight percent of yttrium. In yet other embodiments, the composition can include about 1.0 weight percent of calcium or about 0.6 weight percent of calcium. In still other embodiments, the composition can include less than about 0.5 weight percent of zirconium, or about 0.4 weight percent of zirconium.

Without intending to be bound by any particular theory, it is believed that the presence of yttrium contributes to the improved mechanical strength and corrosion resistance of the biodegradable, metal alloy-containing compositions. Calcium is used in a low quantity to prevent oxidation during the casting of the alloy. Zirconium is known to act as a grain refiner and is used to improve mechanical properties of the compositions.

In another embodiment of the invention, the biodegradable, metal alloy-containing compositions of the invention include the following components: zinc, zirconium and magnesium. The amount of each of these components in the compositions can vary. As previously indicated, in general, the amounts of each of these components are selected in order that the resulting compositions are within acceptable non-toxic limits and are degradable over an acceptable period of time. In certain embodiments, the composition of the invention includes from about 1.0 weight percent to about 6.0 weight percent of zinc, from greater than zero to about 1.0 weight percent of zirconium, and the remainder or balance being magnesium based on the total weight of the composition. In another embodiment, the composition can include about 4.0 weight percent of zinc. In still another embodiment, the composition can include less than about 0.5 weight percent of zirconium.

As described previously herein, the use of magnesium-containing compositions in a physiological environment results in the evolution or production of hydrogen gas. The degradation of magnesium involves a process (i.e., a corrosion process) in which hydrogen is released. In the invention, the amount of magnesium is specified such that the corrosion rate corresponds to a rate of hydrogen formation which is acceptable such that large amounts of hydrogen bubbles do not form and accumulate within a body of a patient.

In certain embodiments, the amounts of yttrium, calcium, zirconium and magnesium are specified and adjusted such as to control at least one of corrosion resistance, biodegradation, biocompatibility, toxicity, cell attachment, mechanical strength and flexibility. In other embodiments, the amounts of zinc, zirconium and magnesium are specified and adjusted such as to control at least one of corrosion resistance, biodegradation, biocompatibility, toxicity, cell attachment, mechanical strength and flexibility.

Further, in certain embodiments, other compounds may be added to impart additional characteristics and properties to the resulting biodegradable, metal alloy-containing compositions. For example, silver may be added to provide anti-microbial properties.

Non-limiting examples of medical devices in which the compositions and articles of the invention can be used include, but are not limited to plates, meshes, staples, screws, pins, tacks, rods, suture anchors, tubular mesh, coils, x-ray markers, catheters, endoprostheses, pipes, shields, bolts, clips or plugs, dental implants or devices, graft devices, bone-fracture healing devices, bone replacement devices, joint replacement devices, tissue regeneration devices, cardiovascular stents, intercranial aneurism device, tracheal stents, nerve guides, surgical implants and wires. In a preferred embodiment, the medical devices include fixation bone plates and screws, temporamandibular joints, cardiovascular stents, and nerve guides.

The medical devices described herein can have at least one active substance attached thereto. The active substance can be either attached to the surface or encapsulated within. As used herein, the term "active substance" describes a molecule, compound, complex, adduct and/or composite that exhibits one or more beneficial activities such as therapeutic activity, diagnostic activity, biocompatibility, corrosion, and the like. Active substances that exhibit a therapeutic activity can include bioactive agents, pharmaceutically active agents, drugs and the like. Non-limiting examples of bioactive agents that can be incorporated in the compositions, articles and devices of the invention include, but are not limited to, bone growth promoting agents such as growth factors, drugs, proteins, antibiotics, antibodies, ligands. DNA, RNA, peptides, enzymes, vitamins, cells and the like, and combinations thereof.

It is contemplated that additional components may be added to the biodegradable, metal alloy-containing compositions of the invention provided that the non-toxicity and biodegradability of the compositions is maintained within acceptable limits. The additional components can be selected from a wide variety known in the art and can include one or more of cerium, aluminum, strontium, manganese and silver.

In certain embodiments, aluminum is present in an amount of from about 1.0 to 9.0 weight percent based on total weight of the composition. In other embodiments, the aluminum is present in an amount of about 2.0 weight percent based on total weight of the composition.

In certain embodiments, manganese is present in an amount of from about 0.1 to about 1.0 weight percent based on total weight of the composition. In other embodiments, the manganese is present in an amount of about 0.2 weight percent based on total weight of the composition.

In certain embodiments, silver is present in an amount of from about 0.25 to about 1.0 weight percent based on total weight of the composition. In other embodiments, the silver is present in an amount of about 0.25 weight percent based on total weight of the composition.

In certain embodiments, cerium is present in an amount of from about 0.1 to about 1.0 weight percent based on total weight of the composition. In other embodiments, the cerium is present in an amount of about 0.5 weight percent based on total weight of the composition.

In certain embodiments, strontium is present in an amount of from about 1.0 to about 4.0 weight percent based on total weight of the composition. In other embodiments, the strontium can be present in an about of 3.0 weight percent.

In one embodiment, the biodegradable, metal-alloy containing composition includes from about 0.5 weight percent to about 4.0 weight percent of ytrrium, from greater than zero to about 1.0 weight percent of calcium, from about 0.25 weight percent to about 1.0 weight percent of silver, from about 0.25 weight percent to about 1.0 weight percent of zirconium, and a balance of magnesium, based on total weight of the composition.

In one embodiment, the biodegradable, metal-alloy containing composition includes from about 0.5 weight percent to about 4.0 weight percent of ytrrium, from greater than zero to about 1.0 weight percent of calcium, from about 0.1 weight percent to about 1.0 weight percent of cerium, from about 0.25 weight percent to about 1.0 weight percent of zirconium, and a balance of magnesium, based on total weight of the composition.

In one embodiment, the biodegradable, metal-alloy containing composition includes from about 0.5 weight percent to about 4.0 weight percent of ytrrium, from greater than zero to about 1.0 weight percent of calcium, from about 0.25 weight percent to about 1.0 weight percent of silver, from about 0.1 weight percent to about 1.0 weight percent of cerium, from about 0.25 weight percent to about 1.0 weight percent of zirconium, and a balance of magnesium, based on total weight of the composition.

In one embodiment, the biodegradable, metal alloy-containing composition includes from about 1.0 to about 6.0 weight percent of zinc, from about 0.25 to about 1 weight percent of silver, from greater than zero to about 1.0 weight percent of zirconium, and a balance of magnesium, based on total weight of the composition.

In one embodiment, the biodegradable, metal alloy-containing composition includes from about 1.0 to about 6.0 weight percent of zinc, from about 0.1 to about 1 weight percent of cerium, from greater than zero to about 1.0 weight percent of zirconium, and a balance of magnesium, based on total weight of the composition.

In one embodiment, the biodegradable, metal alloy-containing composition includes from about 1.0 to about 6.0 weight percent of zinc, from about 0.25 to about 1 weight percent of silver, from about 0.1 to about 1 weight percent of cerium, from greater than zero to about 1.0 weight percent of zirconium, and a balance of magnesium, based on total weight of the composition.

In certain embodiments, the compositions of the invention are devoid of zinc and aluminum. In another embodiment, the compositions of the invention are devoid of aluminum. In still another embodiment, the compositions of the invention may contain an amount of zinc and/or an amount of aluminum that is such as to maintain the toxicity levels of the compositions within acceptable limits. It is known that the presence of zinc and/or aluminum in particular amounts can produce an undesirable or unacceptable level of toxicity in a physiological environment, such as a body of a patient.

The biodegradable, metal alloy-containing compositions of the invention can be prepared using various methods and processes. In general, melting and casting methods and processes are employed. It is known in the art of metallurgy that casting is a production technique in which a metal or a mixture of metals is heated until molten and then, poured into a mold, allowed to cool, and thereby solidify. In certain embodiments, the melted or molten metal or mixture of metals is poured into the mild steel/copper mold at room temperature to 500° C.

Casting of the compositions of the invention can be affected by using any casting procedure known in the art, such as, but not limited to, sand casting, gravity casting, permanent mold casting, direct chill casting, centrifugal casting, low/high pressure die casting, squeeze casting, continuous casting, vacuum casting, plaster casting, lost foam casting, investment casting, and lost wax casting. It is believed that the particular process used for casting can affect the properties and characteristics of the cast composition. Further, it is believed that the temperature at which the melting procedure is performed can also affect the composition. Thus, the temperature may be carefully selected so as to maintain the desired composition of the alloy.

In certain embodiments of the invention, yttrium, calcium, zirconium and magnesium components (in specified amounts described herein) are melted by heating at an elevated temperature, preferably under a protective atmosphere, and then poured into a mold, allowed to cool and solidify. In another embodiment of the invention, zinc, zirconium and magnesium components (in specified amounts described herein) are melted by heating at an elevated temperature, preferably under a protective atmosphere, and then poured into a mold, allowed to cool and solidify.

In certain embodiments, prior to solidification, the molten mixture is tested to determine the amount of the various components therein and therefore, to provide an opportunity to adjust the amounts as desired prior to solidification.

In other embodiments, the melting and/or casting steps are/is performed under a protective atmosphere to preclude, minimize or reduce oxidation/decomposition of the components in the composition. In particular, it is desirable to preclude, minimize or reduce the oxidation/decomposition of magnesium in the composition. The protective atmosphere can include compounds selected from those known in the art, such as but not limited to, argon, sulfur hexafluoride, carbon dioxide, dry air and mixtures thereof.

In yet other embodiments, subsequent to the casting process, the magnesium-containing cast is subjected to homogenization. Without intending to be bound by any particular theory, it is believed that a homogenization treatment can cause the spreading of, or more even or uniform distribution of, impurities, secondary phase(s), and intermetallic phases, if present therein.

In further embodiments, the resulting cast can be subjected to various forming and finishing processes known in the art. Non-limiting examples of such processes include, but are not limited to, extrusion, forging, rolling, equal channel angular extrusion, stamping, deep-drawing, wire-drawing, polishing (by mechanical and/or chemical means), surface treating (to form a superficial layer on the surface) and combinations thereof.

The resulting cast can be formed, finished, machined and manipulated to produce articles and devices for use in medical applications, such as medical devices for implantation into a body of a patient. Furthermore, these medical devices can be used in orthopedic, craniofacial and cardiovascular applications.

Detailed exemplary procedures for performing the melting and casting processes are depicted in the following examples.

The biodegradable, metal alloy-containing compositions of the invention can be used to produce various articles, such as medical devices suitable for implantation into a body of a patient. In preferred embodiments, the medical implant devices include orthopedic, craniofacial and cardiovascular devices.

Additional objects, advantages and novel features of the invention may become apparent to one of ordinary skill in the art based on the following examples, which are provided for illustrative purposes and are not intended to be limiting.

EXAMPLES

Example 1

1.1 Material Preparation

Ingots of elemental magnesium (99.97% pure from U.S. Magnesium, Inc.), calcium (99.5% pure from Alfa-Aesar) and magnesium-yttrium master alloy (4 wt. % yttrium from GKSS in Germany) were weighed according to the nominal composition. The ingots were melted together in a graphite crucible (200 g batch) inside a quartz tube of a vacuum induction furnace to preclude oxidation of the pure elements. The graphite crucible preloaded with batch and the quartz tube assembly were purged with UHP argon several times and vacuumed subsequently to achieve a moisture-free environment prior to induction melting. The induction melting then was conducted and repeated several times in order to achieve compositional homogeneity. The initial alloy produced by the induction melting was cleaned thoroughly from any residue or oxide scale and re-melted subsequently in a mild steel crucible using an electrical resistance furnace (from Wenesco, Inc.). The melting and pouring temperature was about 700° C., and once the temperature was reached, an equivalent amount of zirconium was added using Zirmax® (Mg-33.3% Zr) master alloy (from Magnesium Elektron, LTD.). The liquid melt was stirred for about 10 seconds after 1-minute and 5-minute intervals to dissolve and disperse the zirconium particles uniformly into the melt. The melt was held for about 30 minutes at 700° C. and then poured onto a copper mold (1.5"×0.5") and a steel mold (2.0"×1.5") at room temperature. The as-cast samples were solution treated ("T4") at 525° C. for about 2 hours inside a tubular furnace covered with magnesium gettered powder under a protective atmosphere of argon and sulfur hexafluoride, and then quenched into water. Thin square plates ($10\times10\times1$ mm$^3$) of samples were sectioned (using a Buehler Precision Saw Simplimet 1000) from the as-cast and the T4 samples, and were characterized by X-ray diffraction (XRD) using Philips XPERT PRO system employing the CuKα ($\lambda$=1.54056 Å) radiation operated at 45 kV and 40 mA to determine the phase evolution and formation. The thin plate samples from the as-cast and T4 conditions were also used for electrochemical corrosion, cytotoxicity and cell adhesion tests. Each square plate sample was mechanically grinded and polished to 2000 grit; ultrasonically cleaned in acetone, absolute ethanol and distilled water; and then dried in a vacuum oven at a temperature of 50° C. For cytotoxicity tests, samples were sterilized by ultraviolet radiation for about 1 hour.

1.2 Cytotoxicity Test

A murine osteoblastic cell line (MC3T3-E1) was obtained from American Type Culture Collection ("ATCC", Rockville, Md.) and used in the in vitro experiment to determine the viability of cell attachment to WXK 10 alloys. The cells were cultured in Modified Eagle's Medium alpha (αMEM), 10% Fetal Bovine Serum (FBS), 100 U ml$^{-1}$ penicillin and 100 μg ml$^{-1}$ streptomycin, and incubated at a temperature of 37° C. in a humidified atmosphere with 5% $CO_2$. The alloy samples were incubated in MEM for about 10 minutes after which the cells were seeded on the as-cast and T4 samples, as well as, as-rolled AZ31 control samples, at a cell density of $4\times10^4$ cells/well. After 24 hours of culturing at 37° C. in a humidified atmosphere with 5% $CO_2$, the media was removed and the live/dead cell viability assay was performed using a commercially available kit (obtained from Invitrogen Corporation. Karlsruhe, Germany). This kit was designed to determine the viability/cytotoxicity of cells by differentiating between live and dead cells with fluorescence microscopy of two different colors. The live/dead solution was composed of PBS, ethidium homodimer-1 (EthD-1) and calcein AM. After incubation in the live/dead solution for about 30 minutes at room temperature, images of the live and dead cells were captured using fluorescence microscopy. The excitation wavelength of 495 nm was used for the fluorescence imaging microscopy. The live cells were observed as green (515 nm) fluorescent by enzymatic conversion of calcein AM to labeled calcein. The dead cells were displayed as red (635 nm) by fluorescence enhancement upon entering and binding EthD-1 to nucleic acid due to low membrane integrity.

1.3 Direct Cell Adhesion Test

Following the live/dead cytotoxicity test, the samples were rinsed in Phosphate Buffer Solution (PBS, pH=7.4), fixed in 2.5% glutaraldehyde solution for about 15 minutes at room temperature, rinsed 3 times with the PBS, followed by dehydration in a gradient ethanol/PBS mixture (30%, 50%, 70%, 90%, 95%, 100%) for about 10 minutes each and then, dried. The surface of the cell attached samples were observed using Philips XL-30 FEG scanning electron microscopy (SEM).

1.4 Results

A XRD pattern was generated of the Mg-1% Y-0.6% Ca-0.4% Zr alloy (WXK11) cast into two different molds (i.e. Cu mold and steel mold). It was evident from the XRD pattern that only the α-Mg phase formed during solidification. During alloy design, the alloying additions (Y, Ca) were chosen within their maximum solid solubility limits according to the established phase diagrams to minimize the microgalvanic corrosion path in the biological environment of αDMEM primarily between the matrix and the secondary phase(s). The maximum solid solubility of calcium is 1.12 wt % at 517° C. and for yttrium, 11.4 wt % at 567.4° C. The XRD pattern clearly showed the formation of α-Mg without any traces of intermetallics during solidification of the liquid melt from the pouring temperature (700° C.). Similarly, XRD analysis of the samples which were solution treated at an elevated temperature (525° C.) for about 2 hours also confirmed the absence of any secondary phase(s) and predominantly, the XRD line patterns were indexed with α-Mg.

The osteoblastic MC3T3-E1 cells were cultured in direct αMEM for 24 hours and then, stained with calcein-AM and EthD-1. It was evident upon observation that the number of cells cultured in the negative control cell culture dish and the rolled AZ31 plates remained live after about 24 hours with few dead cells stained in red. However, the cell density decreased in rapid manner in the AZ31 plates which suggested that ionic dissolution, e.g. of $Mg^{2+}$ and $Ca^{2+}$, likely started early with a slight increase in pH value recorded from 7.5 to 8. The WXK10 samples which were cast into two different molds showed improved results when compared with AZ31 as the cell density was more evenly distributed. The solution treated (T4) sample showed an appreciable increase in the cell density covering most of the surface as compared to the as-cast samples. There was no significant difference in the shape of the viable cells (green) between the control and the studied samples groups. Only a few apoptotic cells (red fluorescence bound to nucleic acids) were seen in each group.

Example 2

2.1 Material Preparation

Ingots of elemental magnesium (99.97% pure from U.S. Magnesium, Inc.), zinc (99.99% pure from Alfa-Aesar) were melted together in a mild steel crucible inside an electrical resistance furnace (Wenesco Inc.). A typical melt size was 200 g. The melt was covered with a protective gas atmosphere (0.5% $SF_6$ with the balance Ar) to prevent magnesium burning. Once the desired pouring temperature (700° C.) was reached, an equivalent amount of zirconium was added using Zirmax® (Mg-33.3% Zr) master alloy (from Magnesium Elektron, LTD.). The liquid melt was stirred for about 10 seconds after 1-minute and 5-minute intervals to dissolve and disperse the zirconium particles uniformly into the melt. The melt was held for about 30 minutes at 700° C. and then poured onto a copper mold (1.5"×0.5") at room temperature. The as-cast samples were solution treated ("T4") at 350° C. for about 1 hour inside a tubular furnace under a protective atmosphere of gettered argon and sulfur hexafluoride, and then quenched into water. Thin square plates (10×10×1 $mm^3$) of samples were sectioned (using a Buehler Precision Saw Simplimet® 1000) from the as-cast and the T4 samples, and were characterized by x-ray diffraction (XRD) using Philips XPERT PRO system employing the CuK® ($\lambda$=1.54056 Å) radiation operated at 45 kV and 40 mA to determine the phase evolution and formation. The thin plate samples from the as-cast and T4 conditions were also used for electrochemical corrosion, cytotoxicity and cell adhesion tests. Each square plate sample was mechanically grinded and polished to 2000 grit; ultrasonically cleaned in acetone, absolute ethanol and distilled water; and then dried in a vacuum oven at a temperature of 50° C. For cytotoxicity tests, samples were sterilized by ultraviolet radiation for about 1 hour.

2.2 Cytotoxicity Test

A murine osteoblastic cell line (MC3T3-E1) was obtained from American Type Culture Collection ("ATCC", Rockville, Md.) and used in the in vitro experiment to determine the viability of cell attachment to ZK40 alloys. The cells were cultured in Modified Eagle's Medium alpha (αMEM), 10% Fetal Bovine Serum (FBS), 100 U $ml^{-1}$ penicillin and 100 μg $ml^{-1}$ streptomycin, and incubated at a temperature of 37° C. in a humidified atmosphere with 5% $CO_2$. The alloy samples were incubated in αMEM for about 10 minutes after which the cells were seeded on the as-cast and T4 samples, as well as, as-rolled AZ31 control samples, at a cell density of 4×10$^4$ cells/well. After 24 hours of culturing at 37° C. in a humidified atmosphere with 5% $CO_2$, the media was removed and the live/dead cell viability assay was performed using a commercially available kit (obtained from Invitrogen Corporation, Karlsruhe, Germany). This kit was designed to determine the viability/cytotoxicity of cells by differentiating between live and dead cells with fluorescence microscopy of two different colors. The live/dead solution was composed of PBS, ethidium homodimer-1 and calcein AM. After incubation in the live/dead solution for about 30 minutes at room temperature, images of the live and dead cells were captured using fluorescence microscopy. The excitation wavelength of 495 nm was used for the fluorescence imaging microscopy. The live cells were observed as green (515 nm) fluorescent by enzymatic conversion of calcein AM to labeled calcein. The dead cells were displayed as red (635 nm) by fluorescence enhancement upon entering and binding EthD-1 to nucleic acid due to low membrane integrity.

2.3 Direct Cell Adhesion Test

Following the live/dead cytotoxicity test, the samples were rinsed in Phosphate Buffer Solution (PBS, pH=7.4), fixed in 2.5% glutaraldehyde solution for about 15 minutes at room temperature, rinsed 3 times with the PBS, followed by dehydration in a gradient ethanol/PBS mixture (30%, 50%, 70%, 90%, 95%, 100%) for about 10 minutes each and then, dried. The surface of the cell attached samples were observed using Philips XL-30 FEG scanning electron microscopy (SEM).

2.4 Results

A XRD pattern was generated of the Mg-4% Zn-0.5% Zr alloy (ZK40) cast into a copper mold. It was evident from the XRD pattern that only the α-Mg phase formed during solidification. The amount of zinc added was within the maximum solubility limit of zinc, i.e., 6.2 wt % at a temperature of 341° C. according to the accepted phase diagram. The zinc dissolved into the α-Mg lattice increased the solid-solution strengthening of the alloy.

The osteoblastic MC3T3-E1 cells were cultured in direct αMEM for 24 hours and then stained with calcein-AM and EthD-1. It was evident that the number of cells cultured in the negative control cell culture dish and the rolled AZ31 plates remained live after about 24 hours with few dead cells stained in red. However, the cell density decreased in rapid manner in the AZ31 plates which suggested that ionic dissolution, e.g., of $Mg^{2+}$ and $Ca^{2+}$, likely started early with a slight increase in pH value recorded from 7.5 to 8. The ZK40 sample which was cast into the copper mold, as well as the heat-treated one (300° C., 1 hour) showed improved results when compared with AZ31 as the cell density was more evenly distributed. There was no significant difference in the shape of the viable cells (green) between the control and the studied samples groups. Only a few apoptotic cells (red fluorescence bound to nucleic acids) were seen in each group.

The morphology of the MC3T3-E1 cells was observed at different magnifications (100×, 200×, 1000×, 2000×) after 24 hour incubation in the αMEM medium after fixing the cells in 2.5% glutaraldehyde solution for about 15 minutes. The cells were attached to the surface of the sample and it was evident that cells started growing. The cell spreading was uniform with filopodium and lammelipodium formations which suggested that the as-cast sample was stable in the bio-corrosive environment for cell growth and proliferation.

Example 3

In this example, yttrium (Y), calcium (Ca), zinc (Zn), silver (Ag) and zirconium (Zr) were alloyed in solid solution with magnesium (Mg) to create new Mg alloys. It is believed that Y contributed to grain boundary strengthening of the magnesium alloys as well as improving corrosion resistance with Y content above 3%, Ca improved corrosion resistance and mechanical properties of pure Mg up to 1 wt % Ca. Silver (Ag) provided anti-microbial properties, and Zr served as an effective grain refining agent, imparting grain boundary strengthening and corrosion resistance. Density functional theory has shown alloying with Ca and Y help to form a stable and chemically less reactive hydroxide layer to impart greater corrosion resistance. The alloys in this example, Mg-1Y-0.6Ca-0.4Zr (wt. %), denoted henceforth as WXK11 (codified according to ASTM B275-05), and Mg-4Y-0.6Ca-0.4Zr (wt. %), denoted henceforth as WXK41, were assessed based on their biocompatibility, corrosion behavior, and mechanical properties with the objective of use in orthopedic medical implants. Biocompatibility was determined in vitro using direct and indirect cell viability tests. Corrosion behavior was evaluated electrochemically and using hydrogen evolution. Mechanical properties were measured by both compressing and tensile loading. The novel alloys were compared in their as-cast and T4 solution heat treated conditions, exhibiting improved biocompatibility, corrosion resistance, and mechanical properties as compared to pure Mg.

3.1 Material Preparation and Characterization

Novel magnesium, Mg-based polycrystalline, amorphous alloys were developed using conventional gravity/permanent mold casting, high energy mechanical milling, powder metallurgy and pulsed laser deposition technique. The alloying elements (Zn, Ca, Y, Ce, Ag, Zr, Al, MnSr) were carefully selected based on the first principle theoretical calculation using Vienna ab-initio Simulation Package (VASP) and composition was selected keeping the constituent solute elements (Zn, Ca, Y, Ce, Ag, Zr, Al, Mn, Sr) within the maximum solid solubility (Cs) limit at the liquidus temperature ($T_L$) of the established phase diagrams to impart an equiaxed microstructure. The following compositions were explored in developing novel polycrystalline magnesium alloys: ZK series: Mg-1-6% Zn-0.25-1% Zr, ZQK series: Mg-1-6% Zn-0.1-1% Ag-0.25-1% Zr, ZQEK series: Mg-1-6% Zn-0.1-1% Ag-0.1%-1% Ce-0.25-1% Zr, WXK series: Mg-1-4% Y-0.3-1% Ca-0.25-1% Zr, WXQK series: Mg-1-4% Y-0.3-1% Ca-0.1-1% Ag-0.25-1% Zr, WXEK series: Mg-1-4% Y-0.3-1% Ca-0.1-1% Ce-0.25-1% Zr, WXQEK series: Mg-1-4% Y-0.3-1% Ca-0.1-1% Ag-0.1-1% Ce-0.25-1% Zr, AZXM series: Mg-1-9% Al-0.5-6% Zn-0.3-1% Ca-0.1-1% Mn, AZXMQ series: Mg-1-9% Al-0.5-6% Zn-0.3-1% Ca-0.1-1% Mn-0.1-1% Ag, AZXMW series: Mg-1-9% Al-0.5-6% Zn-0.3-1% Ca-0.1-1% Mn-1-4% Y, AZXMEseries: Mg-1-9% Al-0.5-6% Zn-0.3-1% Ca-0.1-1% Mn-0.1-1% Ce JX series: Mg-1-4% Sr-0.3-1% Ca alloys, JZ series: Mg-1-4% Sr-1-6% Zn alloys, JZX series: Mg-1-4% Sr-1-6% Zn-0.3-1% Ca alloys, JZQX: Mg-1-4% Sr-1-64% Zn 0.1-1% Ag-0.3-1% Ca alloys, JZXQEseries: Mg-1-4% Sr-1-6% Zn0.1-1% Ag-0.3-1% Ca-0.1-1% Ce, JZXQW: Mg-1-4% Sr-1-6% Zn0.1-1% Ag-0.3-1% Ca1-4% Y Pure elemental ingots of Mg (US Magnesium Inc., Salt Lake City, Utah, 99.97%), Ca shots (Alfa-Aesar, Ward Hill, Mass., 99.5%). Zn granules (Alfa-Aesar 99.99%), Al shots (Alfa-Aesar 99.99%). Mn shots (Alfa-Aesar 99.9%), Ag (Alfa-Aesar 99.95%), Mg-5 wt % Ce master alloy, and Mg-4 wt % Y master alloy (Helmholtz-Zentrum Geesthacht Centre for Materials and Coastal Research, Germany) at varying compositions discussed above were weighed according to the nominal composition and melted together in a graphite crucible inside an induction furnace (MTI Corporation, Richmond, Calif.), purged with ultrahigh-purity Ar and vacuumed to avoid oxidation of the pure elements. The initial alloy produced by induction melting was cleaned thoroughly from any residue or oxide scale and re-melted subsequently in a mild steel crucible using an electrical resistance furnace (Wenesco Inc., Chicago, Ill.) under the protection of Ar+1.5% $SF_6$ cover gas. The melting and pouring temperature was between 700-850° C., and once the temperature was reached, an equivalent amount of zirconium was added using Zirmax® (Mg-33.3% Zr) master alloy (Magnesium Elektron Ltd., Manchester, UK). The melt was stirred and held for 30-60 minutes and then poured into a cylindrical steel mold preheated to a temperature of 300-500° C. with an inner diameter of 44 mm. The as-cast samples were solution treated (T4) at a temperature of 300-550° C. for a period of 2-24 hours inside a tubular furnace covered under continuous Ar flow and quenched in water. A few selected alloys were also artificially aged (T6 treatment) in an oil bath between a temperature of 150-300° C. for a period of 12-72 hours. The alloy nominal compositions, determined by inductively coupled plasma optical emission spectroscopy (ICP-OES, iCAP duo 6500 Thermo Fisher, Waltham. Mass.), are listed in Table 1.

TABLE 1

Chemical Composition Obtained from ICP-AES Analysis of Mg—Y—Ca—Zr, Mg—Zn—Zr, and Mg—Y—Ca—Ag—Zr Alloys (wt. %)

| Alloy | Chemical compositions (wt. %) | | | | | | | | |
|---|---|---|---|---|---|---|---|---|---|
| | Y | Ca | Zr | Cu | Fe | Mn | Ni | Si | Mg |
| (WXK11) Mg—1Y—0.6Ca—0.4Zr | 0.66 ± 0.03 | 0.52 ± .01 | 0.13 ± 0.004 | 0.016 | 0.003 | 0.008 | 0.008 | 0.006 | Balance |
| (WXK41) Mg—4Y—0.6Ca—0.4Zr | 3.28 ± 0.001 | 0.42 ± 0.002 | 0.08 ± 0.001 | 0.015 | 0.014 | 0.006 | 0.003 | 0.007 | Balance |

| Alloy | Chemical compositions (wt. %) | | | | | | | |
|---|---|---|---|---|---|---|---|---|
| | Zn | Zr | Cu | Fe | Mn | Ni | Si | Mg |
| (ZK40) Mg—4Zn—0.5Zr | 4.28 ± 0.11 | 0.36 ± 0.008 | 0.014 | 0.002 | 0.003 | 0.018 | 0.007 | Balance |

| Alloy | Chemical compositions (wt. %) | | | | | | | | |
|---|---|---|---|---|---|---|---|---|---|
| | Y | Ca | Ag | Zr | Cu | Fe | Mn | Ni | Mg |
| (WXQK11) Mg—1Y—0.6Ca—0.25Ag—0.4Zr | 0.51 ± 0.017 | 0.49 ± .022 | 0.21 ± 0.005 | 0.182 ± 0.018 | 0.014 | 0.004 | 0.008 | 0.010 | Balance |

Square plate samples (10×10×1 mm$^3$) were sectioned using a diamond saw (Precision Saw Simplimet 1000, Buehler, Lake Bluff, Ill.) from the as-cast and the T4 samples for phase and microstructure characterization, electrochemical corrosion, and direct in vitro cell culture studies. Rod samples of 6 mm diameter and 6 mm length were machined indirect in vitro cell studies. Rod samples of 10 mm diameter and 20 mm length were machined for compressive tests. As-cast Mg (US Magnesium, Inc.) was used as a comparison.

Phase characterization was conducted by X-ray diffraction (XRD) using Philips X'Pert PRO diffractometer employing CuK$_\alpha$ ($\lambda$=1.54056 Å) radiation with a Si-detector (X'celerator). The X-ray generator operated at 45 kV and 40 mA at a 2θ range of 10-90°. Samples were mechanically ground and polished up to 1200) grit, ultrasonically cleaned in isopropyl alcohol, and air dried. For cytotoxicity tests, samples were sterilized by ultraviolet radiation for 1 hour.

3.2 Microstructure Characterization

Square plate samples of the ZK, WXK, WXQK alloy series were mounted in epoxy (EpoxiCure, Buehler), mechanically polished (Tegramin-20, Struers, Ballerup, Denmark), and chemically etched in a solution of 5 mL acetic acid, 6 g picric acid, 10 mL water, and 100 mL ethanol. The microstructure was observed under an optical microscope (Axiovert 40 MAT, Carl Zeiss, Jena, Germany).

3.3 Mechanical Properties

Samples were machined along the long axis of the various alloy ingots in accordance with ASTM-E8-04 for tensile testing and ASTM-E9-09 for compressive testing. Sample dimensions for tensile and compressive testing were as follows: standard dogbone specimens (tensile measurements: gauze length: 12.3 mm, gauze cross-section: 3 mm×3 mm); (compressive measurements: 10 mm dia×20 mm length). Tensile and compressive stress-strain curves were obtained for as-cast and T4 solution treated alloys, and compared to as-cast pure Mg. The tensile and compressive tests were conducted at room temperature at a cross-head speed of 2 mm/min using an Instron universal testing system with laser extensometer by OrthoKinetic® Testing Technologies. Yield strength (YS), Ultimate Tensile Strength (UTS), Young's modulus (E) during compression and tension, percent elongation (%), compressive yield strength, compressive peak strength, percent compression of various alloys was determined from the stress-strain curves. The tensile and compressive yield strengths were determined from the linear portion of the stress-strain curve during the tensile and compressive tests.

3.4 Electrochemical Corrosion Test

To test corrosion of the ZK, WXK, WXQK alloys, the potentiodynamic polarization technique was used. Samples were connected to a copper wire using silver epoxy and mounted in epoxy resin. The mounted samples were mechanically polished, sonicated in isopropyl alcohol, and dried in air. The potentiodynamic corrosion study was carried out with an electrochemical workstation (CH-604A, CH Instruments, Inc., Austin, Tex.) at a scanning rate of 1 mV/s and potential window of 500 mV above and below the open circuit potential. A three electrode cell was employed with platinum as the counter electrode. Ag/AgCl as the reference electrode, and the sample mounted in epoxy resin as the working electrode. The test was performed in Dulbecco's Modified Eagle Medium (DMEM, with 4.5 g/L glucose, L-glutamine, and sodium pyruvate, Cellgro, Manassas, Va.) supplemented with 10% fetal bovine serum (FBS) at pH 7.2±0.2 and held at 37.4° C. Before each measurement, the sample was immersed in DMEM to provide stability. The cathodic and anodic portions of the generated Tafel plots were fit linearly to allow calculation of corrosion potential, $E_{corr}$, and corrosion current density, $i_{corr}$. Samples were cleaned by immersion in 200 g/L of chromic acid and 10 g/L of AgNO$_3$ for 10 minutes to remove corrosion products and corrosion morphology was characterized using SEM and EDX.

3.5 Immersion Corrosion Test (Weight Loss)

Immersion tests were carried out in conformation with ASTM G31-72 (the ratio of surface area to solution volume was 1 cm$^2$:20 ml). Samples were removed after 1 and 3 weeks of immersion, rinsed with distilled water and dried at room temperature. The samples were cleaned by immersion in 200 g/L of chromic acid and 10 g/L of $AgNO_3$ for 10 minutes to remove corrosion products and the degradation rates (in units of mm/year) were obtained according to ASTM-G31-72. The corrosion rate is given by Eq. (1):

Corrosion rate=$(K \times W)/(A \times T \times D)$      Eq. (1)

wherein the coefficient K=$8.76 \times 10^4$, W is the weight loss (g), A is the sample area exposed to solution ($cm^2$), T is the exposure time (h) and D is the density of the material (g $cm^{-3}$). The pH value of the solution was also recorded during the immersion tests.

3.6 Indirect Cytotoxicity Tests

ZK, WXK, WXQK alloy samples and as-cast pure magnesium were polished up to 1200 grit, ultrasonically cleaned in isopropyl alcohol, air dried, and sterilized by ultraviolet radiation for 1 hour. The specimens were incubated in modified Eagle's medium alpha ($\alpha$MEM) supplemented with 10% fetal bovine serum (FBS), 100 U/ml penicillin, and 100 µg/ml streptomycin at a temperature of 37° C. in a humidified atmosphere with 5% $CO_2$ for a period of 72 hours. The sample weight to extraction medium ratio was 0.2 g/mL in accordance with the EN ISO standard 10933:12. This extraction ratio was designated as 100% extract, with less concentrated extracts prepared by diluting the 100% extract into 50%, 25%, and 10% extract solutions. Extracts were sterile filtered using 0.2 µm syringe filter before being added to cells.

The murine osteoblastic cell line (MC3T3-E1, American Type Culture Collection, Rockville, Md.) was used in in vitro cell cytotoxicity experiments, cultured in modified Eagle's medium alpha ($\alpha$MEM), 10% fetal bovine serum, 100 U/ml penicillin and 100 µg/ml streptomycin at a temperature of 37° C. in a humidified atmosphere with 5% $CO_2$. The cells were seeded in 96-well cell culture plates at $6 \times 10^3$ cells/200 µl medium in each well and incubated for 24 hours to attach before adding the extraction medium. The controls used culture medium without extract as the negative control and 10% DMSO culture medium as the positive control. The medium was then replaced with 200 µl of extraction medium at 100%, 50%, 25%, and 10% extract concentrations and incubated under cell culture conditions for 3 days. The cytotoxicity of the corrosion extracts were tested using the MTT assay. Media and extracts were replaced with fresh cell culture medium to prevent interference of the magnesium in the extract from interacting with the tetrazolium salt. The MTT assay was performed according to the Vybrant MTT Cell Proliferation Kit (Invitrogen Corporation, Karlsruhe, Germany) by first adding 10 µl of 12 mM 3-(4,5-Dimethylthiazol-2-yl)-2,5-diphenyltetrazolium bromide (MTT) dissolved in phosphate buffer solution (PBS, pH=7.4) to each well. The samples were incubated at a temperature of 37° C. with MTT for 4 hours, after which 100 µl formazan solubilization solution (SDS-HCl solution) was added to each well and incubated for 12 hours. The absorbance of the samples was measured using the Synergy 2 Multi-Mode Microplate Reader (BioTek Instruments, Winooski, Vt.) at a wavelength of 570 nm. The absorbance of the samples was divided by the absorbance of the mean positive control subtracted from the mean negative control to determine percent viability of cells compared to the controls.

3.7 Direct Cell Viability and Adhesion Test

MC3T3-E1 cells were cultured directly on ZK40, WXK11, WXK41, WXQK11 alloys and as-cast pure magnesium. Cell culture conditions and media were the same as in the indirect cytotoxicity test. Samples were cut to dimensions of 10 mm×10 mm×1 mm and polished up to 1200 grit, ultrasonically cleaned in acetone, air dried, and sterilized by ultraviolet radiation for 1 hour. The alloy samples were incubated in $\alpha$MEM with 10% fetal bovine serum (FBS), 100 U/ml penicillin, and 100 µg/ml streptomycin for 10 minutes after which cells were seeded on the samples at a cell density of $4 \times 10^4$ cells/mL. Viability of the seeded cells was evaluated at 1 and 3 days using the LIVE/DEAD Viability/Cytotoxicity Kit (Invitrogen Corporation, Karlsruhe, Germany) following manufacturer protocol. This kit determines the viability/cytotoxicity of cells by differentiating between live and dead cells with fluorescence microscopy of two different colors. Briefly, the alloy samples with attached MC3T3-E1 cells were washed with PBS and stained for 30 minutes at room temperature with 2 µmol/L ethidium homodimer-1 and 4 µmol/L calcein AM in PBS. After incubation in the Live/Dead solution for 30 minutes in room temperature, live and dead cells images were captured using fluorescence microscopy.

3.8 Results

XRD patterns of the ZK40, WXK11, WXK41 and WXQK11 in as-cast and solution treated (T4) condition were generated. The XRD patterns clearly showed all the alloys were composed of $\alpha$-Mg with an hcp crystal structure, without the presence of unalloyed Y, Ca, Zn, Zr and other intermetallic compounds. The XRD patterns clearly showed that only $\alpha$-Mg solid solution single phase was formed during solidification in the final microstructures. During alloy design, the alloying elements e.g., (Y, Ca, Zn, Zr) were carefully selected within the solid solubility limits at the liquidus temperature (T) of the phase diagrams with the consideration that the final microstructure should be free of any $2^{nd}$ phase/intermetallic phases along the grain boundary regions which are highly cathodic in nature and accelerate microgalvanic corrosion in a suitable physiological environment primarily between the matrix and the secondary phase (s). Chemical composition of each of the alloys was determined by ICP-AES analysis. Table 1 showed that the actual composition of each alloy was within its nominal composition. However, slight decrease in the yttrium, calcium, and zinc was likely due to a re-melting process. It was believed that the loss in total zirconium content was primarily due to settling of large zirconium particles and clusters in the liquid melt. The impurity content of each of the alloy compositions was very low ensuring improved biocompatibility and degradation properties.

Optical micrographs of ZK40, WXQK11, WXK11 and WXK41 alloys in the as-cast and solution treated conditions were generated. The grain size was calculated using a linear-intercept method [ASTM E112]. The average grain size of ZXK40, WXQK11, WXK11, WXK41 alloys in as-cast condition were 60 µm, 130 µm, 110 µm, 80 µm, respectively, with the presence of uniform equiaxed $\alpha$-Mg grains throughout the microstructure. However, the slight presence of secondary phase(s) was also evident along the grain boundary due to second phase(s) precipitates during solidification which is a common phenomenon during casting. The WXK as-cast ingot samples were subjected to solution heat treatment at elevated temperature (525° C.-6 hours) followed by quenching in water to impart a more uniform, homogeneous microstructure. The microstructure after T4 treatment of WXK11, WXK41 alloys showed that there was a slight increase in grain size likely due to coalescence of smaller grains together along the triple point grain boundary regions and formation of supersaturated α-Mg grains after the precipitates dissolved into the matrix.

Table 2 summarizes the mechanical properties of the as-cast and T4 treated alloys herein as compared with commercial AZ31 and pure Mg. Table 2 shows the Young's modulus of the new alloys (E ~64 GPa for ZK40, 51 GPa for WXK11, 38 GPa for WXK41, 51 GPa for WXQK11) were comparable with commercial AZ31 sheet (55 GPa) suggesting that the stiffness of the alloys are sufficient for orthopedic fixation and craniofacial and cardiovascular device applications. However, the new alloys demonstrated surprisingly low value in the yield strength, and ultimate tensile strength as compared to AZ31. It is believed that a potential reason for low value in tensile strength was the presence of casting defects/inclusion in the microstructure. In order to improve the strength and ductility, the alloys were solution treated at elevated temperature and immediately quenched into water to improve the ductility and better shape forming ability in expense of mechanical strength. Although there was a slight increase in elongation, a drastic drop in yield strength and tensile strength was evident.

TABLE 2

Mechanical Properties of As-Cast and T4 Treated Alloys

| Alloy | Young's Modulus (GPa) | Yield Strength (MPa) | Ultimate Tensile Strength (MPa) | Compressive Strength (MPa) | Percent Elongation (%) |
|---|---|---|---|---|---|
| Commercial AZ31 | 55 | 202 | 268 | 409 | 12 |
| Pure Mg | 5 | 19 | 66 | 180 | 7 |
| ZK40 as-cast | 64 | 96 | 176 | 363 | 4 |
| ZK40 T4 | 68 | 92 | 83 | 355 | 1.5 |
| WXK11-as cast | 51 | 72 | 123 | 296 | 3 |
| WXK11-T4 | 49 | 45 | 106 | 226 | 4 |
| WXK41-as cast | 38 | 89 | 162 | 306 | 6 |
| WXK41-T4 | 34 | 44 | 83 | 227 | 3.5 |
| WXQK11-as cast | 51 | 63 | 130 | 300 | 4 |
| WXQK11-T4 | 33 | 45 | 114 | 284 | 6.6 |

The potentiodynamic corrosion behavior of the ZK40, WXK11, WXK41, and WXQK11 alloys in as-cast and solution treated condition along with as-cast pure Mg was studied extensively under physiological condition. The potentiodynamic polarization curves (Tafel plot) of the various samples and pure Mg, recorded at a scan rate of 1 mV/s in the presence of DMEM, were plotted. The cathodic branch of the tafel plot showed the hydrogen evolution through a reduction process whereas the anodic branch represented the magnesium dissolution by oxidation. The cathodic plateaus of pure Mg suggested that the hydrogen evolution started at 1.7 V. However, the calculation of corrosion current density, $i_{corr}$ tabulated in Table 3, clearly showed that the corrosion current density of the ZK40, WXK11, WXK41, and WXQK11 alloys were comparable to pure Mg (30.68 A cm$^{-2}$) and commercial rolled AZ31 sheets (19.20 μA cm$^{-2}$). The corrosion potential, $E_{corr}$ of the ZK40, WXK11, WXK41, WXQK11 were 500 mV higher compared to pure Mg which indicated that the samples were more stable in DMEM, due to formation of a protective film of corrosion product and subsequent passivation of the samples. One noticeable difference was the decrease in the $i_{corr}$ value of solution treated samples compared to as-cast samples (see Table 3) likely due to formation of supersaturated phase and reduction in the volume fraction of secondary phase(s) observed along the grain boundary which can act as cathodic sites for corrosion and also the presence of Zn, Y, Zr which are able to elevate the corrosion potential in the anodic sites resulted improve corrosion rate. The present corrosion study clearly showed that the current alloys are stable in aggressive physiological condition.

TABLE 3

Electrochemical Corrosion Measurements (Using Tafel Plots) Data of Various Alloy

| Material | Corrosion potential, $E_{corr}$ (V) vs. Ag/AgCl (R.E.) | Corrosion current density, $i_{corr}$ (μA cm$^{-2}$) | Corrosion rate (mm/year) |
|---|---|---|---|
| Pure Mg | −1.62 | 30.68 | 0.70 |
| Commercial AZ31 | −1.48 | 19.20 | 0.43 |
| ZK40 as-cast | −1.49 | 39.69 | 0.90 |
| ZK40 T4 | −1.55 | 39.32 | 0.87 |
| WXK11 as-cast | −1.51 | 36.42 | 0.84 |
| WXK11 T4 | −1.41 | 5.70 | 0.13 |
| WXK41 as-cast | −1.56 | 16.70 | 0.5 |
| WXK41 T4 | −1.54 | 5.22 | 0.12 |
| WXQK11 as-cast | −1.61 | 58.88 | 1.35 |

The SEM micrographs of corroded surface of the samples where the corrosion product was cleaned with $CrO_3$/$AgNO_3$ solution were generated. It was evident from the SEM micrographs that corrosion was localized and possibly occurred in the weak grain boundary region which is prone to attack under physiological condition. Formations of small localized cavities throughout the microstructures clearly gave indication that alloy purity and presence of secondary phase/defects are related to controlling and minimizing the degradation rate.

The immersion corrosion plot for ZK40 as-cast and solution treated samples, and for a period of 1 week and 3 weeks, respectively were generated. The corrosion rate was in good agreement with potentiodynamic polarization data (Table 3). However, the exact reason for an increase in corrosion rate over a period of 3 weeks was not clear.

The indirect cytotoxicity results of ZK40 samples were obtained using MC3T3-E1 cells and the MTT assay for 3 days extract. For both culture periods, cell viability was most reduced with 100% extract concentration, and increased as the extract percentage decreased, with no cytotoxicity (>75% viability) observed at 50% or 25% extract concentration. This was consistent with previous findings that showed high extract concentrations were highly cytotoxic and led to osmotic shock, suggesting that a 10-fold extract dilution be used for as-cast magnesium materials.

Cell viability was also studied for WXK11 and WXK41 samples for as-cast and T4 condition with the 1 and 3 days culture time with extracts. After 1 day of culture with extract, both WX11 and WX41 as-cast and T4 treated alloys showed higher cell viability compared to pure Mg at 25% and 10% extract concentration; however, no difference between them could be observed after 3 days of culture.

Osteoblastic MC3T3-E1 cells cultured in direct αMEM for 3 days and then stained with calcein-AM and EthD-1 were obtained. Live cells converted calcein AM to green fluorescent calcein through intracellular esterase activity, while EthD-1 entered cells with compromised membranes where it binded with nucleic acids and produced a bright red fluorescence. ZK40 as-cast sample as well as a solution treated one (350° C.-1 h) showed encouraging results when compared with AZ31 as the cell density was more and evenly distributed. There was no significant difference in the shape of the viable cells (green) between the control and the studied sample groups. Only a few apoptotic cells (red fluorescence in the nuclei) were seen in each group. Morphology of the MC3T3-E1 cells after 3 days incubation in the αMEM medium after fixing the cells in 2.5% glutaraldehyde solution for 15 minutes was generated. The cells were attached on the surface of the sample and it was also evident cell proliferation was already started. The cell spreading was uniform with filopodium and lammelipodium formations which suggested that the as-cast sample was stable in the physiological environment for cell growth and proliferation.

Pre-osteoblast MC3T3-E1 cells were cultured directly on the WX11 and WX41 alloys for 1 and 3 days, and then stained with calcein-AM and ethidium homodimer-1 (EthD-1). After 1 day of culture, both WX11 and WX41 T4 heat treated alloys demonstrated comparable live cell density compared to tissue culture plastic. Pure Mg and the as-cast WX11 and WX41 alloys showed reduced live cell density compared to tissue culture plastic. The WX41 alloys appeared to show higher density of live cells compared to WX11, possibly due to the higher Y content resulting in a more stable corrosion layer on the surface of the alloy. After 3 days of culture, WX11 as-cast and T4 treated as well as the as-cast WX41 alloys demonstrated much lower live cell attachment, consistent with the result of the indirect cytotoxicity test. WX41 T4 treated alloy showed excellent biocompatibility with high live cell attachment throughout the surface of the alloy, far superior to pure Mg and the other WX alloys. The higher cell density on WX41 T4 treated alloy after 3 days demonstrated proliferation of the attached MC3T3-E1 cells.

The invention claimed is:

1. A metal alloy-containing composition, consisting of:
   from about 0.5 weight percent to about 4.0 weight percent of yttrium;
   from greater than zero to about 1.0 weight percent of calcium;
   from about 0.25 weight percent to about 1.0 weight percent of zirconium;
   from about 1.0 weight percent to about 4.0 weight percent of strontium;
   optionally from about 1.0 weight percent to about 9.0 weight percent of aluminum;
   optionally from about 0.1 weight percent to about 1.0 weight percent of manganese;
   optionally from about 0.25 weight percent to about 1.0 weight percent of silver;
   optionally from about 0.1 weight percent to about 1.0 weight percent of cerium;
   and a balance of magnesium and impurities due to production, based on the total weight of the composition,
   wherein the metal alloy-containing composition is used to form a biodegradable, medical implant device.

2. The composition of claim 1, wherein the silver is present in an amount of from about 0.25 weight percent to about 1.0 weight percent based on the total weight of the composition.

3. The composition of claim 1, wherein the cerium is present in an amount of from about 0.1 weight percent to about 1.0 weight percent based on the total weight of the composition.

4. The composition of claim 1, wherein the aluminum is present in an amount from about 1.0 weight percent to about 9.0 weight percent based on the total weight of the composition.

5. A metal alloy-containing composition, consisting of:
   from about 1.0 weight percent to about 6.0 weight percent of zinc;
   from greater than zero to about 1.0 weight percent of zirconium;
   from about 1.0 weight percent to about 4.0 weight percent of strontium;
   optionally from about 1.0 weight percent to about 9.0 weight percent of aluminum;
   optionally from about 0.1 weight percent to about 1.0 weight percent of manganese;
   optionally from about 0.25 weight percent to about 1.0 weight percent of silver;
   optionally from about 0.1 weight percent to about 1.0 weight percent of cerium; and
   a balance of magnesium and impurities due to production, based on the total weight of the composition,
   wherein the metal alloy-containing composition is used to form a biodegradable, medical implant device.

6. The composition of claim 5, wherein the silver is present in an amount of from about 0.25 weight percent to about 1.0 weight percent based on the total weight of the composition.

7. The composition of claim 5, wherein the cerium is present in an amount of from about 0.1 weight percent to about 1.0 weight percent based on the total weight of the composition.

8. A method of preparing a biodegradable, medical implant device, the method comprising:
   melting a metal alloy-containing composition to form a melted magnesium alloy mixture, the metal alloy-containing composition is selected from the group consisting of
   (1) from about 1.0 weight percent to about 4.0 weight percent of strontium, from about 0.5 weight percent to about 4.0 weight percent of yttrium, from greater than zero to about 1.0 weight percent of calcium, from about 0.25 weight percent to about 1.0 weight percent of zirconium, optionally from about 1.0 weight percent to about 9.0 weight percent of aluminum, optionally from about 0.1 weight percent to about 1.0 weight percent of manganese, optionally from about 0.25 weight percent to about 1.0 weight percent of silver, optionally from about 0.1 weight percent to about 1.0 weight percent of cerium, and with a balance of magnesium and impurities due to production, based on the total weight of the composition, and
   (2) from about 1.0 weight percent to about 4.0 weight percent of strontium, from about 1.0 weight percent to about 6.0 weight percent of zinc, from greater than zero to about 1.0 weight percent of zirconium, optionally from about 1.0 weight percent to about 9.0 weight percent of aluminum, optionally from about 0.1 weight percent to about 1.0 weight percent of manganese, optionally from about 0.25 weight percent to about 1.0 weight percent of silver, optionally from about 0.1 weight percent to about 1.0 weight percent of cerium, and with a balance of magnesium and impurities due to production, based on the total weight of the composition; and
   casting said melted magnesium alloy mixture to obtain said biodegradable, medical implant device.

9. The method of claim 8 wherein the metal alloy-containing composition consists of:
from about 1.0 weight percent to about 4.0 weight percent of strontium;
from about 1.0 weight percent to about 6.0 weight percent of zinc;
from greater than zero to about 1.0 weight percent of zirconium, and
the balance is magnesium, based on the total weight of the composition.

10. The method of claim 8, wherein the silver is present from about 0.25 weight percent to about 1.0 weight percent and the cerium is present from about 0.1 weight percent to about 1.0 weight percent based on the total weight of the composition.

11. The method of claim 8, wherein the manganese is present in an amount from about 0.1 weight percent to about 1.0 weight percent based on the total weight of the composition.

12. A biodegradable, medical implant device containing the metal alloy-containing composition of claim 1, wherein the device is selected from the group consisting of an orthopedic device, a craniofacial device and a cardiovascular device.

13. The biodegradable, medical implant device of claim 12, further comprising at least one active substance selected from the group consisting of bone growth promoting agents, drugs, proteins, antibiotics, antibodies, ligands, DNA, RNA, peptides, enzymes, vitamins, cells and combinations thereof.

14. A biodegradable, metal alloy-containing composition, consisting of:
from greater than zero to about 1.0 weight percent of calcium;
from about 0.5 weight percent to about 4.0 weight percent of yttrium;
from about 0.25 weight percent to about 1.0 weight percent of zirconium;
optionally from about 1.0 weight percent to about 4.0 weight percent of strontium;
optionally from about 1.0 weight percent to about 9.0 weight percent of aluminum;
optionally from about 0.1 weight percent to about 1.0 weight percent of manganese;
optionally from about 0.25 weight percent to about 1.0 weight percent of silver;
optionally from about 0.1 weight percent to about 1.0 weight percent of cerium; and
a balance of magnesium and impurities due to production, based on the total weight of the composition.

* * * * *